United States Patent
Takahashi et al.

(10) Patent No.: US 8,236,981 B2
(45) Date of Patent: Aug. 7, 2012

(54) METHOD FOR MANUFACTURING DIALKYLZINC AND DIALKYLALUMINUM MONOHALIDE

(75) Inventors: Hideya Takahashi, Osaka (JP); Tadao Nishida, Osaka (JP); Seijiro Koga, Osaka (JP); Masanori Okutani, Osaka (JP)

(73) Assignee: Nippon Aluminum Alkyls, Ltd. (JP)

( * ) Notice: Subject to any disclaimer, the term of this patent is extended or adjusted under 35 U.S.C. 154(b) by 0 days.

(21) Appl. No.: 12/990,380

(22) PCT Filed: Apr. 30, 2009

(86) PCT No.: PCT/JP2009/058491

§ 371 (c)(1),
(2), (4) Date: Oct. 29, 2010

(87) PCT Pub. No.: WO2009/133929

PCT Pub. Date: Nov. 5, 2009

(65) Prior Publication Data

US 2011/0054206 A1    Mar. 3, 2011

(30) Foreign Application Priority Data

Apr. 30, 2008  (JP) .................................. 2008-118408

(51) Int. Cl.
*C07F 3/00* (2006.01)
*C07F 5/06* (2006.01)

(52) U.S. Cl. .......... 556/129; 556/187; 556/180; 556/186

(58) Field of Classification Search ....................... None
See application file for complete search history.

(56) References Cited

U.S. PATENT DOCUMENTS

| | | | |
|---|---|---|---|
| 3,124,604 | A | 3/1964 | Huther |
| 3,946,058 | A | 3/1976 | Malpass et al. |
| 4,092,342 | A | 5/1978 | Mueller |
| 4,670,571 | A | 6/1987 | Malpass et al. |
| 4,732,992 | A | 3/1988 | Fannin et al. |
| 4,841,082 | A | 6/1989 | Eidt et al. |
| 2005/0283016 | A1* | 12/2005 | Tsudera et al. ............... 556/187 |

FOREIGN PATENT DOCUMENTS

| | | |
|---|---|---|
| BE | 836604 A2 | 4/1976 |
| CA | 1057768 A1 | 7/1979 |
| DE | 2525120 A1 | 1/1976 |
| EP | 0355909 A2 | 2/1990 |
| FR | 2274624 A1 | 1/1976 |
| GB | 1510334 | 5/1978 |
| IT | 1035952 | 10/1979 |
| JP | 37-2026 B | 2/1959 |
| JP | 51-13726 A | 2/1976 |
| JP | 4-221389 A | 8/1992 |
| JP | 4-224584 A | 8/1992 |
| JP | 2863321 B2 | 12/1998 |
| JP | 2863323 B2 | 12/1998 |
| JP | 2003-2892 A | 1/2003 |
| JP | 37-2026 B | 10/2005 |

OTHER PUBLICATIONS

International Search Report for International Application No. PCT/JP2009/058491 mailed Jun. 9, 2009 with English translation.
Office Action for Japanese Application No. 2008-118408, mailed Oct. 18, 2011, with English translation.
The Preparation of the Hydrides of Zinc, Cadmium, Beryllium, Magnesium and Lithium by the Use of Lythium Aluminum Hydride, by Glenn D. Barbaras, Clyde Dillard, A. E. Finholt, Thomas Wartik, K. E. Wilzbach and H. I. Schlesinger, JACS (1951) 73:4585-90.

\* cited by examiner

*Primary Examiner* — Porfirio Nazario Gonzalez
*Assistant Examiner* — James Meadows
(74) *Attorney, Agent, or Firm* — Cantor Colburn LLP

(57) ABSTRACT

A method for manufacturing dialkylzinc and dialkylaluminum monohalide that makes it possible to efficiently manufacture both dialkylzinc and dialkylaluminum monohalide of high purity and at a high yield on an industrial scale with a single reaction from zinc halide and trialkylaluminum as raw materials, while suppressing the production of precipitants in the reaction process and suppressing the adhesion of precipitates to the equipment and the admixture thereof into the product. The method for manufacturing dialkylzinc and dialkylaluminum monohalide by reacting zinc halide with trialkylaluminum, includes using trialkylaluminum with a hydride concentration of 0.01% by mass to 0.10% by mass, and separating dialkylzinc essentially not containing aluminum from reactants and then separating dialkylaluminum monohalide essentially not containing zinc.

7 Claims, 1 Drawing Sheet

METHOD FOR MANUFACTURING DIALKYLZINC AND DIALKYLALUMINUM MONOHALIDE

This is a U.S. national stage application of International Application No. PCT/JP2009/058491, filed on 30 Apr. 2009. Priority under 35 U.S.C. §119(a) and 35 U.S.C. §365(b) is claimed from Japanese Application No. JP2008-118408, filed 30 Apr. 2008, the disclosure of which is also incorporated herein by reference.

TECHNICAL FIELD

The present invention relates to a method for manufacturing dialkylzinc and dialkylaluminum monohalide which can be used for polymerization catalysts, production of pharmaceuticals, solar cells, or the like.

BACKGROUND ART

Dialkylzinc has been conventionally often used as a catalyst or a reaction agent for polymerization or production of pharmaceuticals, or as a substance for forming zinc oxide that forms a transparent conducting film used for electrodes of solar cells or semiconductor devices.

As one of the methods for manufacturing dialkylzinc, a reaction of zinc chloride and trialkylaluminum shown in the equation (1) has been known as described in Patent Documents 1 and 2.

$$ZnCl_2 + 2R_3Al \rightarrow R_2Zn + 2R_2AlCl \qquad (1)$$

In this method, trialkylaluminum ($R_3Al$) as a raw material is a product obtained by reacting aluminum, hydrogen, and an alkene in the presence of trialkylaluminum. The product, however, contains hydrides such as $R_2AlH$, $RAlH_2$, and $AlH_3$ as impurities. As pointed out in Non-Patent Document 1, when trialkylaluminum having a high concentration of a hydride is used as a raw material for the reaction with zinc chloride, a metallic zinc or the like deposit along with the reaction proceed. Further, precipitates deposit during the distillation of dialkylzinc after the reaction. Therefore the precipitates adhere to an inner wall of an apparatus so that the reaction or distillation is forcibly interrupted. In addition to this, there are other problems that it takes a long time to wash the apparatus, and that a heat conduction effect of a heater is reduced.

Here, it is recognized that dialkylaluminum monochloride obtained as a by-product in the reaction of zinc chloride with trialkylaluminum has a catalytic activity for various polymerization reactions, and the demand thereof is increasing.

Dialkylaluminum monochloride is contained in a still residue after dialkylzinc having high volatility is distilled from the reactant solution of the above-mentioned reaction, and can be obtained from this still residue. As mentioned above, however, a large amount of the precipitates such as metallic zinc is contained in the still residue after dialkylzinc is distilled from the reactant solution of the above-mentioned reaction of zinc chloride and trialkylaluminum. Zinc is contained in dialkylaluminum monochloride obtained by distilling this still residue. In addition, similarly to the case of distillation of dialkylzinc, it is difficult to continuously perform distillation separation due to a large amount of precipitates.

Various methods for reducing a concentration of zinc in dialkylaluminum monochloride are reported. Examples thereof include a method for adding trialkylaluminum containing alkylaluminum hydride to a still residue after dialkylzinc is distilled, which is described in Patent Document 3; and a method for adding alkylaluminum sesquichloride to a still residue after dialkylzinc is distilled, which is described in Patent Document 4. However, the boiling point of dialkylaluminum monochloride approximates that of trialkylaluminum or alkylaluminum sesquichloride that have alkyl groups with the same number of carbon atoms, and separation thereof by distillation is difficult.

Furthermore, Patent Document 7 reports a method for heating a still residue at 150 to 240° C. in an inert gas atmosphere after distillation separation of diethylzinc, and Patent Document 8 reports a method for adding aluminum chloride and triethylaluminum to be heated, and subsequently distilling dialkylaluminum monochloride. However, these methods increase the steps. In addition, the concentration of zinc in dialkyl aluminum monochloride obtained is 200 mass ppm or 100 mass ppm or the like, and not sufficiently reduced.

Patent Documents 5 and 6 report use of silicon oxide, water, or the like as an additive as a method for suppressing deposition of metallic zinc in the reaction of zinc chloride with trialkylaluminum. However, it cannot be said that the effect is sufficient, and it is accompanied by a sacrifice of reduction in productive efficiency of dialkylzinc.

In order to obtain trialkylaluminum having a low concentration of a hydride that leads to deposition of metallic zinc, it may be thought that the partial pressure of the alkene as the raw material is increased upon synthesizing trialkylaluminum. However, when the partial pressure of the alkene is increased during synthesizing trialkylaluminum, the alkenes react with the alkyl groups to produce trialkylaluminum having polymeric alkyl groups. By using the produced trialkylaluminum having one or more polymeric alkyl groups as a raw material, dialkylzinc having one or two polymeric alkyl groups is contained in the reactants of the reaction of zinc chloride and trialkylaluminum. The dialkylzinc having one or two polymeric alkyl groups has a boiling point higher than that of dialkylzinc having monomeric alkyl groups, and has a boiling point close to that of dialkylaluminum monochloride. Accordingly, the dialkylzinc having one or two polymeric alkyl groups is mixed with the dialkylaluminum monochloride obtained by distillation separation. For this reason, even if trialkylaluminum which is obtained by increasing the partial pressure of the alkene during synthesizing is used as a row material, a yield of dialkylzinc is reduced and separation of dialkylaluminum monochloride with high purity is difficult.

As mentioned above, in manufacture of dialkylzinc and dialkylaluminum monochloride using zinc chloride and trialkylaluminum as raw materials, a method is demanded in which production of precipitates in the reaction process, and adhesion of precipitates to equipments are suppressed and productivity is not decreased, and both of dialkylzinc and dialkylaluminum monochloride are produced with high purity and yield and on a satisfying industrial scale.

Prior Documents
Patent Documents
[Patent Document 1] JP37-2026B
[Patent Document 2] U.S. Pat. No. 3,124,604
[Patent Document 3] U.S. Pat. No. 4,732,992
[Patent Document 4] U.S. Pat. No. 4,670,571
[Patent Document 5] JP2863321B
[Patent Document 6] JP2863323B
[Patent Document 7] U.S. Pat. No. 3,946,058
[Patent Document 8] U.S. Pat. No. 4,092,342
Non Patent Literature
[Non Patent Document 1] J. Am. Chem. Soc., 73, 4585, 1951

SUMMARY OF INVENTION

Technical Problem

An object of the present invention is to provide a method for manufacturing dialkylzinc and dialkylaluminum monohalide that makes it possible to efficiently manufacture both dialkylzinc and dialkylaluminum monohalide of high purity and at a high yield on an industrial scale with a single reaction from zinc halide and trialkylaluminum as raw materials, while suppressing the production of precipitants in the reaction process and suppressing the adhesion of precipitates to the equipment and the admixture thereof into the product.

Solution to Problem

In order to solve the above-mentioned problems, the present inventors obtained knowledge that in a reaction of zinc halide and trialkylaluminum as the raw materials, by using trialkylaluminum with a hydride in a concentration of 0.01% by mass to 0.10% by mass as a row material, production of precipitates in the reaction process and the distillation process can be suppressed, an amount of precipitates to adhere to equipments is remarkably reduced, and a time to stop manufacturing for washing equipments can be drastically decreased. It was also found out that production of dialkylzinc having one or two polymeric alkyl groups can be suppressed so that dialkylzinc and dialkylaluminum monohalide can be obtained with high purity and at high yield. Based on this knowledge, the present invention has been completed.

Namely, the present invention is a method for manufacturing dialkylzinc and dialkylaluminum monohalide by reacting zinc halide with trialkylaluminum, comprising: using trialkylaluminum with a hydride concentration of 0.01% by mass to 0.10% by mass, and separating dialkylzinc essentially not containing aluminum from reactants and then separating dialkylaluminum monohalide essentially not containing zinc.

ADVANTAGEOUS EFFECTS OF INVENTION

The present invention related to the manufacturing method for dialkylzinc and dialkylaluminum monohalide that makes it possible to efficiently manufacture both dialkylzinc and dialkylaluminum monohalide of high purity and at high yield on an industrial scale with a single reaction from zinc halide and trialkylaluminum starting materials, while suppressing production of precipitates in the reaction process and the distillation process, and suppressing adhesion of the precipitates to equipments and admixture thereof into the products.

DESCRIPTION OF EMBODIMENTS

Figure 1:
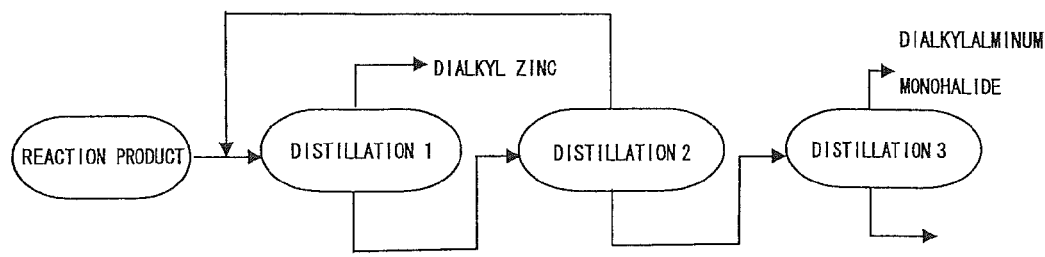
FIG. 1 is a schematic configurational diagram showing an example of the present invention related to a method for manufacturing dialkylzinc and dialkylaluminum monohalide.

The present invention related to dialkylzinc and dialkylaluminum monohalide manufacturing method that causes a reaction between zinc halide and trialkylaluminum, uses trialkylaluminum with a hydride concentration of 0.01% by mass to 0.10% by mass, and separates dialkylzinc essentially not containing aluminum from reactants and then separates dialkylaluminum monohalide essentially not containing zinc.

The present invention related to the method for manufacturing dialkylzinc and dialkylaluminum monohalide uses a reaction of the equation (1X).

$$ZnX_2 + 2R_3Al \rightarrow R_2Zn + 2R_2AlX \tag{1X}$$

wherein X designates a halogen atom and R designates an alkyl group.

The zinc halide, which is one of the raw materials used for the present invention, is solid at normal temperature. Preferably, however, the zinc halide is sufficiently dried because it easily absorbs moisture. The moisture content of the zinc halide is preferably not more than 0.5% by mass, and more preferably not more than 0.1% by mass. Zinc chloride, zinc iodide, and zinc bromide can be cited as examples of the zinc halide, and particularly preferable is zinc chloride.

The trialkylaluminum ($R_3Al$) used for the other raw material, which alkyl groups are not particularly limited, however the alkyl groups have one to five carbon-chain, are preferably used.

The trialkylaluminum is having a hydride concentration of not more than 0.10% by mass, which is referred to as low-hydride trialkylaluminum in some cases. The hydride includes aluminum trihydride ($AlH_3$), monoalkylaluminum dihydride ($RAlH_2$), or dialkylaluminum monohydride ($R_2AlH$). When the trialkylaluminum having the hydride concentration of not more than 0.10% by mass is used, production of precipitates in the reaction is remarkably suppressed, and the amount of the precipitates adhering to an inner wall of equipments is extremely reduced. When the trialkylaluminum having the hydride concentration of less than 0.01% by mass is used, the effect of suppressing production of the precipitates is hardly different from that having the hydride concentration of 0.01% by mass. The trialkylaluminum having hydride concentration of not less than 0.01% by mass has low content of trialkylaluminum having one or more polymerized alkyl groups.

The hydride in trialkylaluminum reacts with water to produce hydrogen, as shown in the equation (2), the equation (3), and the equation (4).

$$AlH_3 + 3H_2O \rightarrow Al(OH)_3 + 3H_2 \tag{2}$$

$$RAlH_2 + 3H_2O \rightarrow Al(OH)_3 + RH + 2H_2 \tag{3}$$

$$R_2AlH + 3H_2O \rightarrow Al(OH)_3 + 2RH + H_2 \tag{4}$$

wherein each R designates an alkyl group.

From the amount of hydrogen produced, the hydride concentration in the trialkylaluminum is determined by the equation (5).

$$\text{Hydride concentration}(\% \text{ by mass}) = d \times (F/3) \times (1/E) \times 100 \tag{5}$$

wherein d, E, and F designate:
d: Molecular weight of aluminum trihydride
E: Mass (g) of a sample
F: Measured value of the number of mols of hydrogen Specifically, in the case where hydrogen produced by reacting 100 g of a sample with water is 22.4 mL at 0° C. and at 1 atmosphere by measurement with gas chromatography, the concentration of the obtained hydride in the sample is 0.010% by mass.

The trialkylaluminum, which has concentration of trialkylaluminum with one or more polymeric alkyl groups of not more than 5.0% by mass, is preferably used. When the trialkylaluminum having the concentration of trialkylaluminum with one or more polymeric alkyl groups of not more than 5.0% by mass is used, production of the dialkylzinc having one or more polymerized alkyl groups can be suppressed, and increase in the content of dialkylzinc having one or two polymerized alkyl groups in dialkylaluminum monohalide obtained by performing distillation separation from reaction products can be suppressed. As a result, a zinc concentration in dialkylaluminum monohalide obtained can be remarkably reduced, and dialkylaluminum monohalide having high industrial utility value can be obtained. Reduction in a yield of dialkylzinc as a target reaction product can also be suppressed.

A value determined by the following method can be used as the concentration of the trialkylaluminum having one or more polymerized alkyl groups in the trialkylaluminum.

Examples of the trialkylaluminum having one or more polymerized alkyl groups can be given as R'$_3$Al, R'$_2$RAl, and R'R$_2$Al, wherein each R' designates a polymerized alkyl group, and each R designates monomeric alkyl group. It is thought that R' is mainly dimeric alkyl group. The trialkylaluminum having one or more polymerized alkyl groups reacts with water to form polymeric alkane, as shown in the equation (6), the equation (7), and the equation (8).

$$R'_3Al + 3H_2O \rightarrow Al(OH)_3 + 3R'H \qquad (6)$$

$$R'_2RAl + 3H_2O \rightarrow Al(OH)_3 + 2R'H + RH \qquad (7)$$

$$R'R_2Al + 3H_2O \rightarrow Al(OH)_3 + R'H + 2RH \qquad (8)$$

From the amount of the polymeric alkane produced, the concentration of trialkylaluminum having one or more polymerized alkyl groups in trialkylaluminum is determined by the equation (9).

$$K = (B/3) \times A \div C \times 100 \qquad (9)$$

wherein K, A, B, and C designate:
K: Concentration of trialkylaluminum having polymerized alkyl groups in trialkylaluminum (% by mass)
B: Measured value of the number of mols of a polymeric alkane (R'H)
A: Molecular weight of trialkylaluminum having three polymerizd alkyl groups (R'$_3$Al) (g/mol)
C: Mass (g) of the sample Here, the amount of the polymeric alkane produced can be measured by gas chromatography.

Such trialkylaluminum can be synthesized by reacting aluminum, hydrogen, and an alkene in the presence of trialkylaluminum to form through an intermediate, as shown in the equations (10) and (11).

$$2Al + 3H_2 + 4(RCH_2CH_2)_3Al \rightarrow 6(RCH_2CH_2)_2AlH \qquad (10)$$

$$(RCH_2CH_2)_2AlH + RCH=CH_2 \rightarrow (RCH_2CH_2)_3Al \qquad (11)$$

wherein each R designates alkyl group or hydrogen atom.

To synthesize trialkylaluminum having a hydride concentration of not more than 0.10% by mass above, an alkene can be reacted with trialkylaluminum having a hydride concentration of approximately 0.40 to 1.0% by mass, which is hereinafter referred to as general trialkylaluminum in some cases. In the general trialkylaluminum to be used, the concentration of trialkylaluminum having one or more polymerized alkyl groups is preferably approximately 1.5 to 3.5% by mass.

When the partial pressure of the alkene is increased in production of the trialkylaluminum, the low-hydride trialkylaluminum can be produced, however the low-hydride trialkylaluminum having one or more alkyl groups composed of polymerized alkanes, mainly dimeric alkanes is increased as shown in the equation (12).

$$(RCH_2CH_2)_3Al + RCH=CH_2 \rightarrow (RCH_2CH_2RCHCH_2)(RCH_2CH_2)_2Al \qquad (12)$$

Therefore, the partial pressure of the alkene in a batch reaction is preferably 0.1 to 0.6 MPa, and more preferably 0.2 to 0.5 MPa. The temperature therein is preferably 50 to 110° C., and more preferably 65 to 95° C. The reaction time is preferably for 1 to 10 hours, and more preferably for 3 to 7 hours. A continuous reaction can be also applied to the reaction.

The above reaction of the trialkylaluminum and the zinc halide can be performed as follows. When moisture exists in a reactor, the trialkylaluminum reacts with the moisture so that the yield of dialkylzinc is reduced. For this reason, the reaction is preferably performed in a dry inert gas atmosphere. The reaction may be performed without a solvent. When the reaction is performed in solvent, a non-aqueous solvent, which does not react with the raw materials and the product, can be used as a dispersion medium. Given taking distillation refining of the reaction products, hydrocarbons having a boiling point higher than the dialkylzinc such as liquid paraffin are more preferable. The amount of the dispersion medium can be, for example, 0.4 to 1.0 based on zinc halide in a mass ratio.

The reaction of the zinc halide and the trialkylaluminum is an exothermic reaction. It is preferable that the reaction is performed at a solution temperature in the range of 20 to 100° C., and more preferably 30 to 70° C. by performing heat removal. At a reaction temperature of not less than 20° C., a reaction rate can be prevented from becoming slow. At a reaction temperature of not more than 100° C., the production of precipitates can be suppressed. For temperature control of the reactor, a method of controlling a raw material feeding flow rate, a refrigerant flow rate, or a refrigerant temperature at the time of feeding can be selected.

As for a proportion of the amounts of the zinc halide and the trialkylaluminum to be used in the above reaction, the trialkylaluminum is preferably 1.6 mol to 2.4 mol based on the zinc halide of 1 mol, and more preferably 1.8 mol to 2.2 mol.

As setting the raw materials in the reactor, it is preferable because of easiness to control the reaction that one of the trialkylaluminum and the zinc halide be first set in the reactor, and the other be gradually fed. When the trialkylaluminum is first set in, the reaction without any dispersed medium is also enabled. By making a raw material feeding rate appropriate, a calorific power per unit time can be prevented from becoming excessively large to raise the solution temperature. As a result, decomposition loss of the dialkylzinc due to the heat can be suppressed. Moreover, preferably, stirring after completing feeding of the raw material is performed for a sufficient period of time until the reaction is completed. Specifically, the time from a start to an end of feeding the raw material to be added to the raw material first set is for 1 to 15 hours and more preferably for 2 to 10 hours. Subsequent stirring is performed for 0.5 to 5 hours, and more preferably for 1 to 3 hours, and the reaction can be completed.

Preferably, separation and refining of the dialkylzinc and the dialkylaluminum monohalide from the reactants after the reaction is completed are performed by distillation. Preferably, before distillation of the reactants, the precipitates contained in the reactants are removed by filtration or the like. Compared with the case where the general trialkylaluminum is used as the trialkylaluminum, the amount of the precipitates is extremely small, and the viscosity of the reactants is reduced in the case where the low-hydride trialkylaluminum is used. Accordingly, filtration using a filter can be performed favorably. The filter made of a metallic mesh can be used suitably, and vertical cylindrical type filter is preferable for easy in handling. The size of an opening of the filter is preferably 10 to 300 μm, and more preferably 40 to 250 μm.

Distillation of the reactants is preferably performed using a distillation column. A distillation method may be use any of a batch method or a continuous method. The suspension of the reactants is transferred to the distillation column, and first, the dialkylzinc is distilled and refined. In order to suppress thermal decomposition of dialkylzinc or dialkylaluminum monohalide, the distillation is preferably performed under reduced pressure. The distillation at not less than 10 Torr is preferable for efficiency of separation. As the distillation separation method for obtaining target the dialkylzinc and the dialkylaluminum monohalide from the reactants with high purity, the following methods are preferable.

A first method is a method for distilling reactants to obtain dialkylzinc with high purity as a distillate, distilling a still residue to separate all dialkylzinc that remains in the still residue on the first distillation as a distillate, and then, distilling a still residue on the second distillation to obtain dialkylaluminum monohalide with high purity as a distillate.

Specifically, examples of the first method can be given a method shown in FIG. 1. In the first method, the dialkylzinc with high purity is distilled from the reactants by the first distillation 1. Then, by the second distillation 2 of the still residue on the first distillation 1, all the dialkylzinc contained in the still residue on the first distillation 1 is distilled and separated and removed from the still residue. By the third distillation 3 of the still residue on the second distillation 2, the dialkylaluminum monohalide contained in the still residue on the second distillation 2 is obtained with high purity.

The first distillation 1 that distills dialkylzinc with high purity from the reactants is performed at a reflux ratio of 0.1 to 10, for example, and more preferably at a reflex ratio of 1 to 5, and at a pressure of 10 to 100 Torr, and more preferably at 20 to 50 Torr. While the temperature of the still liquid is different depending on physical properties of an object to be distilled and pressure, the dialkylzinc is preferably distilled at a temperature not exceeding 150° C. As the composition of the still liquid changes, the temperature of the still liquid is gradually increased. In order to prevent aluminum from being mixed with the distillate of the dialkylzinc, the recovery rate of the dialkylzinc per distillation, namely, the proportion of the dialkylzinc to be distilled is preferably controlled to not more than 95% by mass based on the total mass of dialkylzinc in the reactants. Thereby, the dialkylzinc essentially not containing aluminum and specifically having a concentration of aluminum of not more than 10 mass ppm can be distilled. The still residue of the first distillation 1 is supplied to the second distillation 2.

The second distillation 2 is performed in order to distill and recover all the dialkylzinc that remains in the still residue on the first distillation 1, and to prevent zinc from being mixing into the dialkylaluminum monohalide to be separated from this still residue to obtain the dialkylaluminum monohalide with high purity. This second distillation 2 can be performed subsequent to the first distillation 1. Alternatively, the still residue on the first distillation 1 may be once stored in another tank, the first distillation of the dialkylzinc may be repeated several times, and these still residues on the first distillation added to the stored still residue may be supplied to the second distillation 2. The second distillation 2 can also be performed at a reflux ratio of 0 and at approximately the same pressure and still liquid temperature as those in the first distillation 1. Alternatively, the second distillation of the dialkylzinc can be accelerated by reducing an operating pressure. A distillate on the second distillation 2 is preferably added to reactants of a post batch. The dialkylzinc contained in the distillate on the second distillation 2 can be recovered as a distillate on the first distillation 1. The still residue on the second distillation 2 is supplied to the third distillation 3.

The third distillation 3 aims at obtaining high purity dialkylaluminum monohalide contained in the still residue on the second distillation 2. The third distillation 3 is performed at a reflux ratio of 0.2 to 5, for example, and more preferably at a reflux ratio of 0.5 to 3, and a pressure of 10 to 100 Torr and more preferably at 15 to 50 Torr. While the temperature of the still liquid is different depending on physical properties of an object to be distilled and operating pressure, the third distillation is preferably performed at a temperature not exceeding 250° C. Also in the third distillation 3, by controlling the amount of dialkylaluminum monohalide to be distilled to not more than 95% by mass based on the total mass of the dialkylaluminum monohalide in the distillation column, the dialkylaluminum monohalide essentially not containing zinc, and specifically having a zinc concentration of not more than 10 mass ppm can be obtained. The still residue on the third distillation 3 is discarded.

Next, a second method is a method for distilling reactants and separating all the dialkylzinc as a distillate, distilling the distillate to obtain dialkylzinc with high purity as a distillate, and distilling a still residue on the first distillation to obtain dialkylaluminum monohalide with high purity as a distillate.

Figure 2:
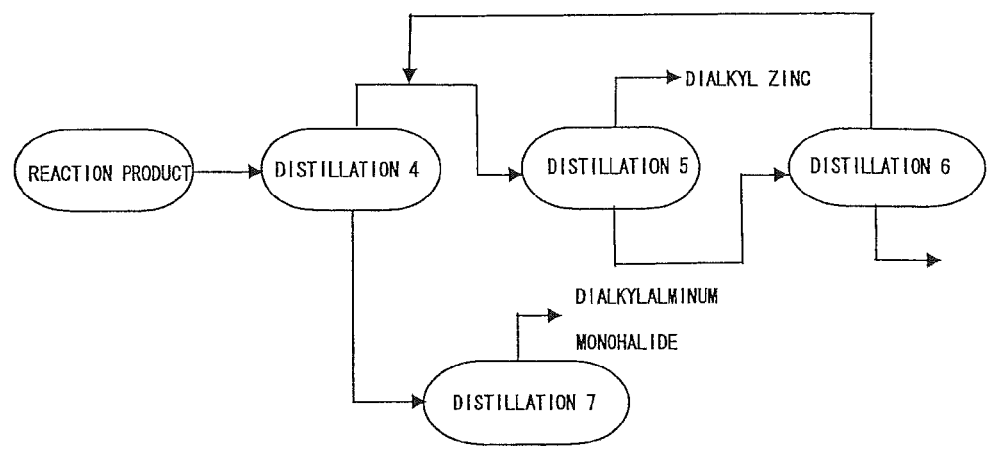
FIG. 2 is a schematic configurational diagram showing another example of the present invention related to a method for manufacturing dialkylzinc and dialkylaluminum monohalide.

Specifically, examples of the second method can be given a method shown in FIG. 2. In the second method, all the dialkylzinc contained in the reactants is distilled by the first distillation 4 of the reactants, and this distillate is subjected to the second distillation 5 to obtain a distillate of the dialkylzinc with high purity. Then, dialkylaluminum monohalide contained in the still residue is obtained with high purity by the third distillation 7 of the still residue on the first distillation.

The first distillation 4 that distills all the dialkylzinc contained in the reactants is performed in order to prevent dialkylzinc from remaining in the still residue of this distillation and to prevent zinc from being mixed with the dialkylaluminum monohalide distilled from this still residue to obtain dialkylaluminum monohalide with high purity. The first distillation 4 is preferably performed, for example, at a reflux ratio of 0 and at a pressure of 10 to 100 Torr and more preferably 20 to 50 Torr. While the temperature of the still liquid is different depending on physical properties of an object to be distilled and pressure, the first distillation 4 is preferably performed at a temperature not exceeding 150° C. As the composition of the still liquid changes, the temperature of the still liquid is gradually increased. The obtained distillate is supplied to the second distillation 5.

The second distillation 5 is performed in order to obtain the dialkylzinc with high purity from the distillate on the first distillation 4. The second distillation 5 is performed at a reflux ratio of 0.5 to 5 and more preferably at a reflux ratio of 1 to 4, at a pressure of 10 to 100 Torr and more preferably at 20 to 50 Torr. In order to prevent aluminum from being mixed in the distillate as dialkylzinc, it is preferable to control the recovery rate of dialkylzinc per distillation, namely, the proportion of the dialkylzinc to be distilled to not more than 95% by mass based on the total mass of dialkylzinc in the distillation column. Therefore, the dialkylzinc essentially not containing aluminum, specifically the dialkylzinc having an aluminum concentration of not more than 10 mass ppm can be distilled. In the second distillation 5, the composition of the still liquid does not largely change, therefore the temperature of the still liquid is approximately constant. The still residue on the second distillation 5 is supplied to the distillation 6.

The distillation 6 is performed in order to distill and recover the dialkylzinc that remains in the still residue on the second distillation 5. This distillation 6 can be performed subsequent to the second distillation 5. Alternatively, the still residue on the second distillation 5 may be once stored in another tank, the second distillation may be repeated several times, and these still residues of the second distillation may be added to the still residue stored in the tank and be supplied to the distillation 6. The distillation 6 can also be performed on the same conditions as those in the first distillation 4. The distillate on the distillation 6 can be added to the distillate on the first distillation 4 for the post batch to perform the second distillation 5. The still residue on the distillation 6 is discarded.

The third distillation 7 is performed in order to distill the still residue on the first distillation 4 to obtain dialkylaluminum monohalide with high purity. The third distillation 7 is performed at a reflux ratio of 0.2 to 5, for example, and more preferably at a reflux ratio of 0.5 to 3, and a pressure of 10 to 100 Torr and more preferably at 20 to 50 Torr. By controlling the amount of dialkylaluminum monohalide to be distilled at not more than 95% by mass based on the total mass of dialkylaluminum monohalide in the distillation column, the dialkylaluminum monohalide essentially not containing zinc, specifically the dialkylaluminum monohalide having a zinc concentration of not more than 10 mass ppm can be obtained. The still residue on the third distillation 7 is discarded.

By the method above, dialkylzinc essentially not containing aluminum, and specifically having an aluminum concentration of not more than 10 mass ppm, and dialkylaluminum monohalide essentially not containing zinc, and specifically having a zinc concentration of not more than 10 mass ppm can be obtained.

EXAMPLES

Hereinafter, Examples will be given to specifically describe the present invention of the method for manufacturing dialkylzinc and dialkylaluminum monohalide.

Example 1

Production of Triethylaluminum

First, a low-hydride triethylaluminum was produced as follows.

Replacement with nitrogen was performed on a 5 m³ stainless steel reactor on which a stirrer, a triethylaluminum supply line, an ethylene supply line, a nitrogen supply line, and a thermometer were mounted, and the pressure in the reactor was retained 0.01 MPaG. Then, 3200 kg of triethylaluminum having a hydride concentration of 0.7% by mass and a trialkylaluminum having one or more butyl groups concentration of 2.1% by mass was supplied to the reactor. The stirrer was operated, and the temperature of the solution was raised to 80° C. Then, ethylene supply was started, and the pressure was retained at 0.39 MPaG. After 4-hour stirring, ethylene supply was stopped, and the solution was cooled. Then, low-hydride triethylaluminum having a hydride concentration of 0.05% by mass and a triethylaluminum having one or more butyl groups concentration of 3.5% by mass was obtained.

[Reaction of Zinc Chloride with Triethylaluminum]

Replacement with nitrogen was performed on a 6 m³ carbon steel reactor on which a stirrer, a zinc chloride supply line, a triethylaluminum supply line, a liquid paraffin supply line, a nitrogen supply line, and a thermometer were mounted, and the pressure in the reactor was retained 0.01 MPaG. Then, 2300 kg of the low-hydride triethylaluminum was supplied to the reactor. While the stirrer was operated, 1400 kg of zinc chloride was supplied to this reactor over 10 hours. During this period of time, cooling water was flown through a cooling water line spirally arranged along a lower part of the reactor to remove reaction heat. The reaction temperature was increased from an initial temperature of 36° C. to 40° C. at most. Supply of zinc chloride was completed, followed by stirring for 2 hours. The pressure of the reactant suspension after the reaction was completed was raised to 0.05 MPaG with nitrogen, and while the reactant suspension was filtered with a 2 m², 100 μm filter, the reactant suspension was transferred to a five-stage sieve tray type distillation column made of carbon steel and having a still volume of 6 m³.

The amount of the precipitates captured was 11.1 kg. The time needed for filtration was 14 minutes, and the average filtration time per kg of the precipitates was 1.3 minutes. In overhaul inspection of the reactor, no precipitates adhering to the stirrer and the inner wall of the reactor was observed. In washing work of the filter, the working time including backwashing with liquid paraffin was 1.5 hours.

[Distillation]

The obtained suspension was distilled.

A heat exchanger that heats the still liquid is a vertical cylindrical multipipe type, has 57 tubes having an inner diameter of 25.4 mm and a length of 3500 mm, and heats a liquid flowing through a tube side by a heating medium on a side of a body. Under a reduced pressure of 30 Torr, the temperature of 3600 kg of the still liquid was gradually raised from 30° C. to 90° C., and the still liquid was distilled. At a reflux ratio of 3, the first distillation 1 and the second distillation 2 were continuously performed. It took 11 hours to obtain 1100 kg of the distillate on the first distillation 1, and it took 5 hours to obtain 500 kg of the distillate on the second distillation 2. In the distillate on the first distillation 1, purity of diethylzinc was not less than 99.9% by mass, and the concentration of aluminum was not more than 10 ppm in mass. In the distillate on the second distillation 2, diethylzinc was 70 kg, and diethylaluminum monochloride was 430 kg.

2000 kg of the still residue on the second distillation 2 was transferred to a tank. After distillation was completed, when overhaul inspection of the inner wall of the still and the heat exchanger was performed, no precipitate adhered to these inner walls. The same operation of the reaction and the first distillation 1 and the second distillation 2 were repeated twice, 4000 kg of the still residue on the second distillation 2 stored in the tank was supplied to the distillation column, and the third distillation 3 was performed under conditions of a pressure of 27 Torr, a still liquid temperature of 144 to 149° C., and a reflux ratio of 1. Over 20 hours, 3500 kg of a distillate was obtained. From analysis of the distillate, purity of diethylaluminum monochloride was not less than 99.9% by mass, and the concentration of zinc was not more than 10 mass ppm. After the distillation was completed, when overhaul inspection of the inner wall of the still and the heat exchanger was performed, no precipitate adhered to these inner walls. Per synthesis, a yield of diethylzinc having an aluminum concentration of not more than 10 mass ppm obtained by the distillation was 1100 kg, and a yield of diethylaluminum monochloride having a zinc concentration of not more than 10 mass ppm obtained by the distillation was 1750 kg.

Example 2

Reaction of Zinc Chloride with Triethylaluminum

To the reactor used in Example 1, 1400 kg of zinc chloride and 930 kg of liquid paraffin were supplied. Replacement with nitrogen was performed on the inside of the reactor. At a pressure of 0.01 MPaG, 2300 kg of the low-hydride triethylaluminum having a hydride concentration of 0.04% by mass and a trialkylaluminum having one or more butyl groups concentration of 3.6% by mass was supplied over 9 hours while cooling water was flown and the stirrer was operated. The reaction temperature was increased from an initial temperature of 36° C. to 41° C. at most. Supply of triethylaluminum was completed, followed by stirring for 2 hours. The pressure of the suspension after the reaction was completed was raised to 0.05 MPaG with nitrogen, and while the suspension was filtered with a 2 m$^2$, 100 μm filter, the reactant suspension was transferred to the distillation column used in Example 1.

The amount of the precipitates captured was 18.5 kg. The time needed for filtration was 25 minutes, and the average filtration time per kg of the precipitates was 1.4 minutes. In overhaul inspection of the reactor, no precipitates adhered to the stirrer and the inner wall of the reactor was observed. In washing work of the filter, the working time including backwashing with liquid paraffin was 1.5 hours.

[Distillation]

The first distillation 4 was performed on 4500 kg of the obtained filtrate under a reduced pressure of 30 Torr, the temperature of the still liquid was gradually raised from 35° C. to 95° C. 1200 kg of a distillate were distilled over 12 hours, and 3300 kg of a still residue remained. The still residue was transferred to a tank. After the distillation was completed, when overhaul inspection of the inner wall of the still and the heat exchanger was performed, no precipitate adhered to these inner walls. The same operation of the reaction and the first distillation 4 were repeated 3 times, and 3600 kg of the distillate stored in the tank was supplied to the distillation column. The second distillation 5 was performed over 50 hours on conditions of a pressure of 30 Torr, a still liquid temperature of 38° C., and a reflux ratio of 3, and 3100 kg of a distillate was obtained. From analysis of the distillate, purity of diethylzinc was not less than 99.9% by mass, and the concentration of aluminum was not more than 10 mass ppm. 500 kg of the still residue remained in the still, and this still residue was transferred to a tank. The second distillation 5 was repeated 3 times, and 1500 kg of the still residues stored in the tank was supplied to the distillation column. Further, 2000 kg of liquid paraffin was added to the distillation column. Then, the distillation 6 was performed under a reduced pressure of 30 Torr and a reflux ratio of 0, while the still liquid temperature was gradually raised from 65° C. to 95° C. Over 10 hours, 1000 kg of a distillate was distilled. Purity of diethylzinc was 99.8% as a result of analysis of the distillate. The still residue 3300 kg on the first distillation 4 was supplied to the distillation column, and the third distillation 7 was performed over 14 hours on conditions of a pressure of 27 Torr, a still liquid temperature of 144 to 149° C., and a reflux ratio of 1. From analysis of 2050 kg of the distillates, purity of diethylaluminum monochloride was not less than 99.9% by mass, and the concentration of zinc was not more than 10 mass ppm. After the distillation was completed, when overhaul inspection of the inner wall of the still and the heat exchanger was performed, no precipitate adhered to these inner walls. Per synthesis, a yield of diethylzinc having an aluminum concentration of not more than 10 mass ppm obtained by the distillation was 1033 kg, and a yield of diethylaluminum monochloride having a zinc concentration not more than 10 mass ppm obtained by the distillation was 2050 kg.

Comparative Example 1

The reaction was performed by the same method as that in Example 1 except that triethylaluminum having a hydride concentration of 0.7% by mass and an alkylaluminum having one or more butyl groups concentration of 2.2% by mass was used. Filtration was performed after the reaction was completed. The amount of the precipitates captured with the filter was 104 kg. Because the solution stopped flowing in the course of filtration, the filtration was performed in 7 steps. Each step of the filtration respectively took 80 minutes, 92 minutes, 110 minutes, 127 minutes, 135 minutes, 158 minutes, and 185 minutes, and took total time of 887 minutes. Clogging was increased as the filtration process advanced, so that the filtration time gradually became longer. The average filtration time per kg of the precipitates was 8.5 minutes. The viscosity of the precipitates was remarkably higher than that in Example 1 in which triethylaluminum having a hydride concentration of 0.05% by mass was used as the raw material and that in Example 2 in which triethylaluminum having a hydride concentration of 0.04% by mass was used as the raw material. The washing work time of the filter including backwashing by liquid paraffin needed an average of 7 hours per filtration step. The filter was used for the next filtration step without the clogging being able to be completely removed. It took 15 hours to distill 3450 kg of the filtrate to obtain 900 kg of a distillate on the first distillation 1, and it took 9 hours to obtain 400 kg of a distillate on the second distillation 2. At a pressure of 30 Torr, the still liquid temperature was increased from 30° C. to 90° C. In the distillate on the first distillation 1, purity of diethylzinc was not less than 99.9% by mass, and the concentration of aluminum was not more than 10 mass ppm. In the distillate on the second distillation 2, diethylzinc was 50 kg and diethylaluminum monochloride was 350 kg. In overhaul inspection of the reactor, it was observed that a large amount of the precipitates firmly adhered to the stirrer and the inner walls of the reactor. Five days were needed for a work to remove and wash this adhering precipitates. It was observed that the precipitates also firmly adhered to the inner wall of the still in the distillation column and the inner wall of the heat exchanger for heating the still liquid. Three days were needed for a work to remove and wash the adhering precipitates in the inner wall of the still in the distillation column and the inner wall of the heat exchanger. A yield of diethylzinc having an aluminum concentration of not more than 10 mass ppm obtained by distillation was 900 kg.

Comparative Example 2

The reaction was performed by the same method as that in Example 1 except that in production of the low-hydride triethylaluminum, triethylaluminum obtained by supplying ethylene to the reactor and reacting for 9 hours at 80° C. while the pressure was retained at 0.53 MPaG and having a hydride concentration of 0.005% by mass and an alkylaluminum having one or more butyl groups concentration of 5.5% by mass was used. Filtration was performed after the reaction was completed. The amount of the precipitates captured with the filter was 12.7 kg. The time needed for filtration was 19 minutes, and the average filtration time per kg of the precipitates was 1.4 minutes. The first distillation 1 and the second distillation 2 were performed on 3600 kg of the filtrate under a reduced pressure of 30 Torr while the still liquid temperature was gradually raised from 30° C. to 90° C. It took 11 hours to obtain 1050 kg of a distillate on the first distillation 1, and it took 5 hours to obtain 500 kg of a distillate on the second distillation 2. In the distillate on the first distillation 1, purity of diethylzinc was not less than 99.9% by mass, and the concentration of aluminum was not more than 10 mass ppm. In the distillate on the second distillation 2, diethylzinc was 70 kg and diethylaluminum monochloride was 430 kg. A still residue 2050 kg was transferred to a tank. After the distillation was completed, overhaul inspection of the inner wall of the still and the heat exchanger was performed. There was no precipitate adhering to these inner walls. The same operation of the reaction and the first distillation 1 and the second distillation 2 were repeated twice, and 4100 kg of the still residue stored in the tank was supplied to the distillation column. The third distillation 3 was performed on conditions of a pressure of 27 Torr, a still liquid temperature of 144 to 149° C., and a reflux ratio of 1 to obtain 3500 kg of a distillate. Purity of diethylaluminum monochloride was 99.9% by mass, and the concentration of zinc was 510 mass ppm. Per synthesis, a yield of diethylzinc having an aluminum concentration of not more than 10 mass ppm obtained by the distillation was 1050 kg, and a yield of diethylaluminum monochloride containing 510 mass ppm of zinc obtained by the distillation was 1750 kg.

Comparative Example 3

The reaction was performed by the same method as that in Example 1 except that in production of the low-hydride triethylaluminum, triethylaluminum obtained by supplying ethylene to the reactor and reacting for 2 hours at 80° C. while the pressure was retained at 0.18 MPaG and having a hydride concentration of 0.13% by mass and an alkylaluminum having one or more butyl groups concentration of 3.1% by mass was used, and the suspension after the reaction was completed was not filtered. The first distillation 1 and the second distillation 2 were performed on 3700 kg of the reaction suspension under a reduced pressure of 30 Torr at a reflux ratio of 3 while the still liquid temperature was gradually raised from 30° C. to 90° C. It took 17 hours to obtain 1000 kg of a distillate on the first distillation 1, and it took 10 hours to obtain 500 kg of a distillate on the second distillation 2. In the distillate on the first distillation 1, purity of diethylzinc was not less than 99.9% by mass, and the concentration of aluminum was not more than 10 mass ppm. In the distillate on the second distillation 2, diethylzinc was 70 kg and diethylaluminum monochloride was 430 kg. A still residue 2100 kg was transferred to a tank. After the distillation was completed, overhaul inspection of the inner wall of the still and the heat exchanger was performed. It was observed that the precipitates also firmly adhered to the inner wall of the still in the distillation column and the inner wall of the heat exchanger for heating the still liquid. Three days were needed for a work to remove and wash the adhering precipitates to the inner wall of the still in the distillation column and the inner wall of the heat exchanger.

TABLE 1

| | Example 1 | Example 2 | Comparative Example 1 | Comparative Example 2 | Comparative Example 3 |
|---|---|---|---|---|---|
| Hydride concentration (% by mass) | 0.05 | 0.04 | 0.7 | 0.005 | 0.13 |
| Concentration of butyl group containing alkylaluminum (% by mass) | 3.5 | 3.6 | 2.2 | 5.5 | 3.1 |
| Liquid paraffin | Not used | Used | Not used | Not used | Not used |
| Amount of precipitates captured with filter (kg) | 11.1 | 18.5 | 104 | 12.7 | Not performed |
| Filtration time (minute) | 14 | 25 | 887 | 19 | Not performed |
| Filtration time per unit precipitates (min/kg) | 1.3 | 1.4 | 8.5 | 1.4 | Not performed |
| Filter washing time (hour) | 1.5 | 1.5 | 49 | 1.6 | Not performed |
| State of adhesion of precipitates in reactor and stirrer | No adhesion | No adhesion | Firm adhesion | No adhesion | No adhesion |
| Working time for washing reactor | | | Five days | | |
| The number of times of distillation | 3 | 4 | 2 | 3 | 2 |
| Content of distillation | DEZ rectification + DEZ recovery distillation + DEAC rectification | DEZ crude distillation + DEZ rectification + DEZ recovery distillation + DEAC rectification | DEZ rectification + DEZ recovery distillation | DEZ rectification + DEZ recovery distillation + DEAC rectification | DEZ rectification + DEZ recovery distillation |
| State of adhesion of precipitates in distillation column and heat exchanger | No adhesion | No adhesion | Firm adhesion | No adhesion | Firm adhesion |
| Washing time for washing distillation colum and heat exchange | | | Three days | | Three days |
| DEZ yield (kg/synthesis) | 1100 | 1033 | 900 | 1050 | 1000 |
| Concentration of aluminum in DEZ (mass ppm) | 10 or less | 10 or less | 10 or less | 10 or less | 10 or less |
| DEAC yield (kg/synthesis) | 1750 | 2050 | Distillation not performed | 1750 | Distillation not performed |

TABLE 1-continued

|  | Example 1 | Example 2 | Comparative Example 1 | Comparative Example 2 | Comparative Example 3 |
|---|---|---|---|---|---|
| Zinc concentration in DEAC (mass ppm) | 10 or less | 10 or less | Distillation not performed | 510 | Distillation not performed |

Descriptions in the table designate the following:
DEZ Diethylzinc
DEAC Diethylaluminum monochloride
DEZ rectification Distillation 1 in FIG. 1 or distillation 5 in FIG. 2
DEZ recovery distillation Distillation 2 in FIG. 1 or distillation 6 in FIG. 2
DEAC rectification Distillation 3 in FIG. 1 or distillation 7 in FIG. 2
DEZ crude distillation Distillation 4 in FIG. 2.

INDUSTRIAL APPLICATION FIELD

The present invention of the method for manufacturing dialkylzinc and dialkylaluminum monohalide can be applied to industrial production to produce products with high purity efficiently. The obtained products can be used for polymerization catalysts, production of pharmaceuticals, solar cells, or the like.

The invention claimed is:

1. A method for manufacturing dialkylzinc and dialkylaluminum monohalide by reacting zinc halide with trialkylaluminum, comprising:
    reacting the zinc halide with the trialkylaluminum to form a mixture containing reaction products, wherein the trialkylaluminum contains aluminum trihydride, a monoalkylaluminum dihydride, a dialkylaluminum monohydride, and combinations thereof at a total concentration of 0.01% by mass to 0.10% by mass;
    distilling the mixture to obtain dialkylzinc containing aluminum in not more than 10 parts per million (ppm) by mass as a first distillate;
    distilling a still residue to separate all remaining dialkylzinc from the still residue as a second distillate; and
    distilling the still residue to separate dialkylaluminum monohalide containing zinc of not more than 10 ppm by mass as a third distillate.

2. The method for manufacturing dialkylzinc and dialkylaluminum monohalide according to claim 1, wherein a concentration of trialkylaluminum having one or more polymerized alkyl groups in the trialkylaluminum is not more than 5.0% by mass.

3. The method for manufacturing dialkylzinc and dialkylaluminum monohalide according to claim 1, wherein the distillate on the second distillation containing all dialkylzinc that remains in the still residue on the first distillation is added to reaction products of a post batch.

4. A method for manufacturing dialkylzinc and dialkylaluminum monohalide by reacting zinc halide with trialkylaluminum, the method comprising:
    reacting the zinc halide with trialkylaluminum to form a mixture containing reaction products, wherein the trialkylaluminum comprises aluminum trihydride, monoalkylaluminum dihydride, dialkylaluminum monohydride, or combinations thereof at a total concentration of 0.01% by mass to 0.10% by mass;
    distilling the mixture to separate all dialkylzinc as a first distillate;
    distilling the first distillate to obtain dialkylzinc containing aluminum in not more than 10 ppm by mass as a second distillate; and
    distilling a still residue on the first distillation to obtain dialkylaluminum monohalide containing zinc in not more than 10 ppm by mass as a third distillate.

5. The method for manufacturing dialkylzinc and dialkylaluminum monohalide according to claim 4, wherein a still residue on the second distillation is distilled to separate all dialkylzinc that remains in the still residue on the second distillation as a distillate, and the distillate is added to a distillate on the first distillation of a post batch.

6. The method for manufacturing dialkylzinc and dialkylaluminum monohalide according to claim 1, wherein the trialkylaluminum is triethylaluminum.

7. The method for manufacturing dialkylkzinc and dialkylaluminum monohalide according to claim 4, wherein the trialkylaluminum is triethylaluminum.

* * * * *